(12) United States Patent
Chen et al.

(10) Patent No.: US 11,367,797 B2
(45) Date of Patent: Jun. 21, 2022

(54) NANOPORE FET SENSOR WITH NON-LINEAR POTENTIAL PROFILE

(71) Applicant: IMEC VZW, Leuven (BE)

(72) Inventors: Chang Chen, Heverlee (BE); Koen Martens, Aalter (BE); Pol Van Dorpe, Spalbeek (BE); Simone Severi, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 16/761,712

(22) PCT Filed: Jul. 24, 2018

(86) PCT No.: PCT/EP2018/070007
§ 371 (c)(1),
(2) Date: May 5, 2020

(87) PCT Pub. No.: WO2019/120642
PCT Pub. Date: Jun. 27, 2019

(65) Prior Publication Data
US 2021/0184053 A1    Jun. 17, 2021

(30) Foreign Application Priority Data
Dec. 22, 2017    (EP) .................................... 17210422

(51) Int. Cl.
*H01L 21/00*    (2006.01)
*H01L 29/786*    (2006.01)
(Continued)

(52) U.S. Cl.
CPC ... *H01L 29/78696* (2013.01); *G01N 27/4146* (2013.01); *H01L 21/308* (2013.01); *H01L 29/1041* (2013.01); *H01L 29/511* (2013.01)

(58) Field of Classification Search
CPC .............. G01N 27/414; G01N 27/4146; H01L 29/511; H01L 29/1041; H01L 29/78696
See application file for complete search history.

(56) References Cited

U.S. PATENT DOCUMENTS

2010/0066348 A1* 3/2010 Merz .................... C12Q 1/6869
324/71.1
2010/0327847 A1 12/2010 Leiber et al.
(Continued)

FOREIGN PATENT DOCUMENTS

JP    2014-190891 A    10/2014

OTHER PUBLICATIONS

Xie, Ping, Qihua Xiong, Ying Fang, Quan Qing, and Charles M. Lieber. "Local electrical potential detection of DNA by nanowire-nanopore sensors." Nature nanotechnology 7, No. 2 (2012): 119-125.
(Continued)

*Primary Examiner* — Reema Patel
(74) *Attorney, Agent, or Firm* — McDonnell Boehnen Hulbert & Berghoff LLP

(57) ABSTRACT

In a first aspect, the present invention relates to a nanopore field-effect transistor sensor (100), comprising: i) a source region (310) and a drain region (320), defining a source-drain axis; ii) a channel region (330) between the source region (310) and the drain region (320); iii) a nanopore (400), defined as an opening in the channel region (330) which completely crosses through the channel region (330), oriented at an angle to the source-drain axis, having a first orifice (410) and a second orifice (420), and being adapted for creating a non-linear potential profile between the first (410) and second (420) orifice.

20 Claims, 7 Drawing Sheets

(51) Int. Cl.
*G01N 27/414* (2006.01)
*H01L 21/308* (2006.01)
*H01L 29/10* (2006.01)
*H01L 29/51* (2006.01)

(56) References Cited

U.S. PATENT DOCUMENTS

2016/0033451 A1  2/2016  Suehle et al.
2016/0187290 A1  6/2016  Leburton
2016/0231307 A1  8/2016  Xie

OTHER PUBLICATIONS

PCT Search Report and Written Opinion, Application No. PCT/EP2018/070007, dated Oct. 8, 2018, 18 pages.

\* cited by examiner

NANOPORE FET SENSOR WITH NON-LINEAR POTENTIAL PROFILE

CROSS-REFERENCE

This application is a 371 U.S. national phase of PCT/EP2018/070007, filed Jul. 24, 2018, which claims priority from EP 17210422.6, filed Dec. 22, 2017, both which are incorporated by reference in its entirety.

TECHNICAL FIELD OF THE INVENTION

The present invention relates to the field of field-effect transistor (FET) sensors; more particularly to nanopore field-effect transistor sensors.

BACKGROUND OF THE INVENTION

Biosensors have been developed intensively during the last decades and have enabled a wide set of applications in life sciences. As a very special biosensors, nanopore sensors provide the unique advantage of single molecule sensitivity; thereby having a great potential for single molecule studies and DNA sequencing. A first sequencing strategy by means of a nanopore is based on electrophoresis driven DNA translocation through the nanopore and subsequently monitoring the blockade effect of DNA on the ionic current flow through this nanopore. The underlying nucleotide sequence information may then be derivable from the fluctuations of the resulting signals.

Revealing this sequence, however, requires the solving of several fundamental problems. Major challenges include: (1) to extract the correct sequence information, for which sensitivity and accuracy at the single nucleotide level are required; (2) to effectively control the molecular motions; (3) to obtain a high throughput readout, and (4) to fabricate reliable devices. In the past decades, many different paths have been tried and developed to overcome these problems.

A first approach is based on the use of transmembrane protein channels (not to be confused with the channel region of the FET) as bio-nanopores. Bio-nanopores offer the specific advantage of an extremely well-defined shape, size and local charge distribution and the possibility to engineer these parameters using established molecular engineering technologies. In addition, bio-nanopores can be combined relatively easily with other biochemical technologies to control DNA motion. As such, bio-nanopore sensing has achieved a noticeable success and is, up to now, the only commercialized nanopore approach for deciphering genomes and other biomedical applications. However, drawbacks of this technique are the susceptible lipid membrane and bio-nanopores and the weak current signals (~pA) preventing the move towards higher throughput and robustness.

Therefore, considerable research was performed on alternative nanopores, especially solid-state nanopores. Different solid-state nanopore technologies have been developed and show feasibility on single-molecular sensing, but none can solve all challenges, especially the intrinsic conflicts between current intensity, spatial resolution, and sensitivity.

Xie et al. (2012) have shown that a solid-state nanopore combined with a synthesized silicon nanowire field-effect transistor (FET) can detect single molecules based on the fluctuations of local liquid potential during DNA translocations (Xie, Ping, et al. "Local electrical potential detection of DNA by nanowire-nanopore sensors." Nature nanotechnology 7.2 (2012): 119-125). Rather than modulating the ionic current through the pore, the blockade effect caused by DNA translocations can thus directly change the distribution of the local fluidic potentials inside the pore and sequentially modulate and amplify the transistor current of a FET near the pore; comparable to gating in a traditional FET. Potential sensing through transistors is an active method and avoids the need for a highly sensitive and passive measurement of the corresponding ionic current. Xie et al. reported that the transistor current (~60 nA) was considerably larger than its corresponded ionic current (~4 nA) through the same pore. This offers significant advantages, especially with respect to the scalability of the measurement technique. Ionic measurements need stable electrodes (one pair per nanopore), strict galvanic separation between different conductive channels and highly sensitive current amplifiers. In contrast thereto, modulating the signal in a transistor circuit with the nanopore potential has the ability to overcome some of these challenges.

Other results on this type of nanopore read-out have been based on 2D materials, such as graphene and $MoS_2$. Although these materials indeed have very interesting properties, they still lack the maturity of the silicon platform, making it difficult to achieve a parallelized read-out scheme with millions of nanopores per chip.

There is thus still a need in the art for nanopore field-effect transistor sensors with a sufficient sensitivity and sufficient spatial resolution, which can be manufactured in such a way as to allow parallelization and fast sampling rates.

SUMMARY OF THE INVENTION

It is an object of the present invention to provide a good nanopore field-effect transistor sensor. It is a further object of the present invention to provide good methods for making said nanopore field-effect transistor sensor. The above objective is accomplished by products, methods and uses according to the present invention.

It is an advantage of embodiments of the present invention that a nanopore field-effect transistor sensor with a large sensitivity (e.g. sufficient to identify single molecules) can be obtained.

It is an advantage of embodiments of the present invention that a nanopore field-effect transistor sensor with a high spatial resolution (e.g. sufficient to identify single nucleotides in a DNA strand) can be obtained.

It is an advantage of embodiments of the present invention that a relatively large number (e.g. an array) of nanopore field-effect transistor sensors can be formed on a single substrate. It is yet a further advantage of embodiments of the present invention that a relatively large number of sensing actions, of the same or of different analyte solutions, can be performed simultaneously; thereby speeding up the overall measurement to increase the throughput or achieving a higher accuracy in the same time span. It is a further advantage of embodiments of the present invention that the malfunction of a nanopore field-effect transistor in the plurality of nanopore field-effect transistor working in parallel can have a low effect on the overall performance of the device.

It is an advantage of embodiments of the present invention that the nanopore field-effect transistor sensor may be relatively inexpensive to manufacture, even in large numbers.

It is an advantage of embodiments of the present invention that the nanopore field-effect transistor sensor can be made using well-known techniques from semiconductor technology (e.g. CMOS technology). It is a further advantage of embodiments of the present invention that the nanopore field-effect transistor sensor can be made in a way that is compatible with other semiconductor devices and that they can be integrated therewith on a single substrate.

In a first aspect, the present invention relates to a nanopore field-effect transistor sensor, comprising
  i. a source region and a drain region, defining a source-drain axis;
  ii. a channel region between the source region and the drain region;
  iii. a nanopore through the channel region, oriented at an angle to the source-drain axis, having a first and a second orifice, and being adapted for creating a non-linear potential profile between the first and second orifice.

Typically, the potential profile created between the first and second orifice of the nanopore is less linear than the potential profile present between the first and second orifice of a nanopore that would have all of the following characteristics:
  identical first and second orifices (e.g. same area, edges of same chemical nature, same permittivity, same surface charges, same surface chemical functionalization, formed of a material of same thickness), and
  constant cross-section from the first orifice to the second orifice.

Preferably, the nanopore is adapted for creating a non-linear potential profile in the channel region.

In embodiments, the first aspect relates to a nanopore field-effect transistor sensor, comprising
  i. a source region and a drain region, defining a source-drain axis;
  ii. a channel region between the source region and the drain region;
  iii. a nanopore, defined as an opening in the channel region which completely crosses through the channel region, oriented at an angle to the source-drain axis, having a first orifice and a second orifice, and being adapted for creating a non-linear potential profile between the first and second orifice.

In a second aspect, the present invention relates to a nanopore field-effect transistor sensor array, comprising at least 50 nanopore field-effect transistor sensors according to any embodiment of the first aspect, preferably at least 100, yet more preferably at least 1000.

In a third aspect, the present invention relates to a system comprising:
  i. the nanopore field-effect transistor sensor according to any embodiment of the first aspect,
  ii. a first electrolyte solution contacting the first orifice of the nanopore, and
  iii. a second electrolyte solution contacting the second orifice of the nanopore.

In a fourth aspect, the present invention relates to a method for forming a nanopore field-effect transistor sensor, comprising:
  a. providing a structure comprising:
    i. a substrate,
    ii. a source region and a drain region in the substrate, defining a source-drain axis;
    iii. a channel region between the source region and the drain region,
    iv. optionally a layer on the channel region, and
    v. a mask layer over the channel region and the optional layer, the mask layer comprising an opening therethrough overlaying the channel region, the opening having a first width and being oriented at an angle to the source-drain axis;
  b. optionally, shrinking the opening such that the first width is reduced to a second width;
  c. etching the optional layer if present and the channel region through the opening, thereby forming a nanocavity;
  d. optionally, shrinking a width of the nanocavity.
  e. optionally, removing the mask layer;
  f. forming the nanopore from the nanocavity by opening the substrate underneath the nanocavity; the nanopore having a first orifice delimited by a first edge and a second orifice delimited by a second edge;
wherein the nanopore is adapted for creating a non-linear potential profile between the first and second orifice by:
  performing step c of etching the channel region through the opening by anisotropically etching the channel region, and the optional layer if present, in such a way that the first orifice and the second orifice differ in area, and/or by
  modifying the first edge and/or the second edge so that they differ in chemical nature and/or so that they are made of dielectric material differing in thickness.

In embodiments, if no optional layers are present, the nanocavity referred to in step c, d and f, is defined as an opening in the channel region.

In embodiments where optional layers are present, the nanocavity may be defined either as the opening in the channel region or as the opening in the channel region and the optional layers. In embodiments where optional layers are present and the nanocavity is defined as the opening in the channel region, the part of the opening extending in the optional layers is not considered part of the nanocavity.

In a fifth aspect, the present invention relates to a use of a non-linear potential profile for increasing a sensitivity and/or a spatial resolution of a nanopore field-effect transistor sensor. The non-linear potential profile is preferably present in the channel region.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 1 illustrates a representative field-effect transistor (FET) structure (110) comprising a substrate (200) comprising a buried oxide layer (202; e.g. SiO$_2$) on a support layer (201), a channel region (330) on the buried oxide layer (202) in-between two source/drain regions (310,320), source/drain contacts (311,321) to the source/drain regions (310,320) and a dielectric layer (340) conformally covering the channel region (330), source/drain regions (310,320) and source/drain contacts (311,321).

FIG. 2 shows deep (e.g. around 50 to 100 μm deep) dry or wet etching performed to open the bottom of the buried oxide layer (202), through the support layer (202). A freestanding FET structure is thereby obtained.

FIG. 3 shows a hardmask layer (501) (e.g. Al$_2$O$_3$) is deposited over the dielectric layer (340), as part of a mask layer (500).

FIG. 4 shows a photoresist layer (502; e.g. poly(methyl methacrylate)), as part of the mask layer (500), spin coated over the hardmask layer (501).

FIG. 5 shows a small opening (510), e.g. around 20 nm wide, is patterned into the photoresist layer (502), for example using electron-beam lithography, to obtain an intermediate structure (120).

FIG. 6 shows the opening (510) patterned down into the hardmask layer (501) using a dry or wet etching.

FIG. 7 shows the opening (510) is patterned down through the dielectric layer (340) and the channel region (330) using a dry or wet etching; forming a nanocavity (401) in the channel region (330). The etching is performed in such a way that the width of the nanocavity (401) tapers down towards the bottom of the nanocavity (401).

FIG. 8 shows at least the nanocavity (401) conformally lined with a first gate dielectric (610; e.g. SiO$_2$), for example using ALD.

FIG. 9 shows removal of the photoresist layer (502).

FIG. 10 shows the nanocavity (401) filled with a protective material (402; e.g. a resist, a porous material or a solid-state material), in order to safeguard it during the subsequent process steps.

FIG. 11 shows at least part of the buried oxide layer (202) is removed, thereby opening a bottom surface of the channel region (330) and, optionally, of the source/drain regions (310,320).

FIG. 12 shows using a dry or wet etching where the portion of the first gate dielectric (610) extending below the channel region (330) is removed.

FIG. 13 shows removal of the protective material (402) to open up the nanopore (400).

FIG. 14 shows using ALD, evaporation or sputtering, a second gate dielectric (620; e.g. Al$_2$O$_3$) deposited on a bottom surface of the channel region (330) and, optionally, of the source/drain regions (310,320). A nanopore FET sensor (100) is thereby obtained, wherein the first orifice (410) of the nanopore (400) is delimited by the first gate dielectric (610) and the second orifice (420) is delimited by the second gate dielectric (620).

In FIG. 15, part a, a nanopore (400) having a width which tapers uniformly from the first orifice (410) to the second orifice (420) is shown. In FIG. 15, part b, a nanopore (400) with a step-profile is shown; e.g. the width (w) of the nanopore (400) may have one or more discrete locations at which the nanopore width changes, but said width may otherwise be relatively constant. In FIG. 15, part c, a nanopore (400) is shown having a constant width, but comprising subcomponents (431,432) of differing composition; the subcomponents (431,432) may, for example, have a difference in permittivity. In FIG. 15, part d, a nanopore (400) with a step-profile similar to FIG. 15, part b, is shown, but wherein said step-profile is due to the presence of different subcomponents (431,432) akin to FIG. 15, part c. A nanopore (400) in accordance with FIG. 15, part d, may, for example, be obtained by performing a selective epitaxial growth (e.g. selective epitaxial growth of Si) on a subcomponent of one composition (432), selectively with respect to a subcomponents of a different composition (431); thereby obtaining a change in width along the nanopore (400).

In FIG. 16, part a, a nanopore (400) having a first (410) and second (420) orifice both having a circular shape is shown. In FIG. 16, part b, a nanopore (400) with a first (410) and second (420) orifice both having a square shape is shown.

Figure 1:
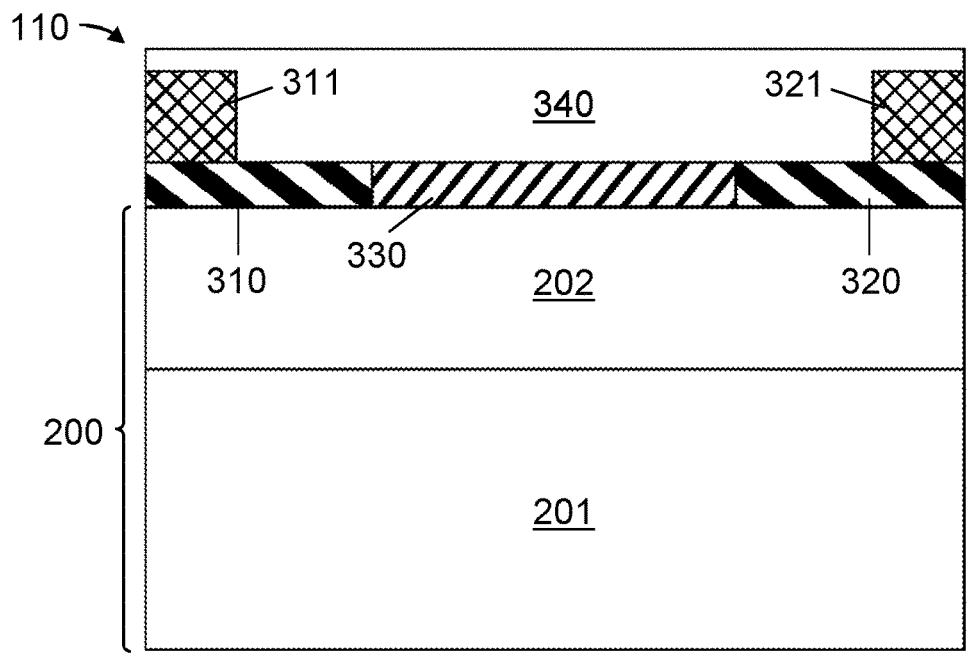
FIGS. 1 to 14 are schematic representations of vertical cross-sections through intermediate structures along the fabrication of a FET sensor, in accordance with an exemplary embodiment of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable with their antonyms under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising" therefore covers the situation where only the stated features are present and the situation where these features and one or more other features are present. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by means of carrying out the function. Thus, an element described herein of an apparatus embodiment is an example of a means for carrying out the function performed by the element for the purpose of carrying out the invention.

In the description provided herein, numerous specific details are set forth. However, it is understood that embodiments of the invention may be practised without these specific details. In other instances, well-known methods, structures and techniques have not been shown in detail in order not to obscure an understanding of this description.

Reference will be made to transistors. These are devices having a first main electrode such as a drain, a second main electrode such as a source and a control electrode such as a gate for controlling the flow of electrical charges between the first and second main electrodes.

The following terms are provided solely to aid in the understanding of the invention.

As used herein, and unless otherwise specified, a nanocavity is an opening in a layer (e.g. in an FET channel or in an FET channel and in one or more overlaying layers such as overlaying dielectric layers) having at least one lateral dimension (width and/or length) ranging from 1 nm to 500 nm, preferably from 1 nm to 100 nm; preferably all dimensions of the nanocavity may range from 1 nm to 500 nm. The nanocavity may, for example, be defined by a width, a length, and a depth (or height), wherein the depth is typically a dimension perpendicular to a surface of the nanocavity-comprising layer. Preferably both width and length may range from 1 nm to 500 nm, preferably from 1 nm to 100 nm. Preferably all of the width, length and depth may range from 1 nm to 500 nm, preferably from 1 nm to 100 nm. The nanocavity is not typically limited by its shape and any cross-section therethrough may typically have any shape (e.g. triangular, rectangular, square, oval, circular, irregular, etc.); for example: an orifice of the nanocavity, co-planar with a surface of the nanocavity-comprising layer, may have any of the aforementioned shapes. In some embodiments, the nanocavity may have a depth smaller than a thickness of the nanocavity-comprising layer, such that a bottom of the nanocavity is defined within said layer. In other embodiments, the nanocavity may have a depth within 5% of the thickness of the nanocavity-comprising layer, while nevertheless having a closed bottom. In yet other embodiments, the nanocavity may completely cross through the nanocavity-comprising layer, thereby having both a top and a bottom of the nanocavity opening up to the surroundings; such a nanocavity is herein referred to as a nanopore. Such a nanopore may, for example, open up to a sensor cavity on one side and open up to another fluidic cavity on the opposite side.

The fact that the nanocavity is an opening in a layer which can be an FET channel and the fact that a nanopore is a nanocavity that completely crosses through the nanocavity-comprising layer, means that in embodiments, a nanopore may be defined as an opening in the FET channel which completely crosses through it.

Since a nanocavity has an orifice which is coplanar with a surface of the nanocavity-comprising layer (e.g. the FET channel), in embodiments where the nanopore is defined as an opening in the FET channel, the nanopore has a first and a second orifice coplanar with respectively a first and a second surface of the FET channel. In embodiments of the present invention, a non-linear potential profile is created between these orifices.

When a layer has an opening therein, said opening varying in section along its depth, said opening having a narrower portion having a section having at least one lateral dimension ranging from 1 nm to 500 nm and a broader portion having a section having both lateral dimensions above 500 nm, only the narrower portion of the opening is considered to be a nanocavity.

As used herein and unless specified otherwise, a layer can be a single layer or can be formed of a plurality of sub-layers.

As used herein, and unless otherwise specified, an asymmetric nanopore is a nanopore having an architecture such that there is no mirror plane between the first and second orifice, oriented perpendicular to an axis therebetween, which would allow the nanopore to be reflected onto itself. An asymmetric nanopore may be preferred in a nanopore field-effect transistor sensor according to the present invention, as it typically allows a potential profile, which is created between a first and a second orifice of the nanopore during operation of the sensor, to be non-linear. This is particularly advantageous when the nanopore is defined as an opening in the FET channel because a non-linear potential profile in the channel region, i.e. where the molecule detection occurs, is most effective. In any embodiments, the non-linear potential profile may be present in the channel region.

As used herein, and unless otherwise specified, under 'source/drain' is understood a 'source and/or drain'. Likewise, under 'source/drain entity', e.g. source/drain region, is understood a 'source entity and/or drain entity', e.g. a source region and/or drain region. In embodiments, a source and a drain may be comparable (e.g. indistinguishable) and their designation may depend on a relative voltage difference that is put across them in the final device.

As used herein, and unless otherwise specified, the terms "channel", "FET channel", and "channel region" are used interchangeably and designate, in a semiconductor layer comprising a drain region and a source region, the region of that layer situated between the drain region and the source region. The semiconductor layer comprising the drain region, the source region and the channel region therebetween is sometimes referred to as the active layer of the FET. When the actual path through which charge carriers flow from source to drain is meant, the term "conductive channel" will be used.

In a first aspect, the present invention relates to a nanopore field-effect transistor sensor, comprising
i. a source region and a drain region, defining a source-drain axis;
ii. a channel region between the source region and the drain region;
iii. a nanopore, defined as an opening in the channel region which completely crosses through the channel region, oriented at an angle to the source-drain axis, having a first and a second orifice, and being adapted for creating a non-linear potential profile between the first and second orifice.

The field-effect transistor (FET) sensor may further comprise conventional elements as are well known to the skilled person. In embodiments, the FET sensor may be formed on a semiconductor substrate (e.g. a group IV wafer such as an Si wafer, a silicon-on-insulator substrate or an epitaxial stack). In embodiments, the FET sensor may be formed on a group IV (e.g. Si) or group III-V (e.g. GaN) layer on a semiconductor substrate. Likewise, the source/drain regions may typically be of conventional design. Source and drain contacts may connect to the source/drain regions. The active layer comprising the source region, the drain region and the channel region is a semiconductor active layer such as a group IV active layer and more typically an Si active layer. During operation, an analyte solution may be present in the nanopore and sensing by the FET sensor may be based on gating of the channel current by the analyte. In preferred embodiments, the analyte may be charged. In embodiments, the field-effect transistor sensor may be a chemical sensor, such as a sensor for sensing a chemical (e.g. an ionic species) or a pH, and/or it may be a biological sensor, such as a sensor for sensing a biomolecule (e.g. a nucleotide in a nucleic acid, such as DNA or RNA). A biological sensor may typically be thought of as a specific case of a chemical sensor. In embodiments, the field-effect transistor sensor may be considered to be an ion-sensitive field-effect transistor (ISFET) or a field-effect transistor-based biosensor (BioFET).

In embodiments, the channel region may have a width of from 2 nm to 250 nm, and/or a length of from 2 to 1000 nm, and/or a height of from 0.1 to 50 nm. In embodiments, the channel region may have one or more layers thereon. Preferably, the channel region may have a dielectric layer thereon.

In embodiments, the nanopore field-effect transistor sensor may further comprise a layer, preferably a dielectric layer, on the channel region.

In embodiments where the nanopore is defined as an opening in the FET channel and in one or more overlaying layers, the nanopore may be present at least partly through that layer (e.g. dielectric layer).

In other embodiments where the nanopore is defined as an opening in the FET channel, an extension of the opening through that layer (e.g. dielectric layer) is not considered to be a part of the nanopore for the purpose of the present invention.

In embodiments, the dielectric layer may have a thickness over the channel region of from 1 to 100 nm. In embodiments, at least a portion of the dielectric layer thickness may be a membrane for protecting the channel region from damage or contamination. In embodiments, the nanopore may be lined by a gate dielectric layer. In embodiments, different portions of the nanopore may be lined by different gate dielectric layers. In embodiments, the gate dielectric layer may be selected from $SiO_2$, $Si_3N_4$, $Al_2O_3$, $HfO_2$, $TiO_2$ and $Ta_2O_5$. In embodiments, the gate dielectric layer lining the nanopore may have a thickness inside the nanopore of from 1 to 10 nm. In embodiments, the first orifice may open on a first sensor cavity and/or the second orifice may open on a second sensor cavity. In embodiments where the nanopore is defined as an opening in the FET channel, a first orifice of the nanopore or of an extension thereof in one or more layers may open in a first cavity, and a second orifice of the nanopore or an extension thereof in one or more layers may open in as second cavity. The sensor cavity typically has both lateral dimensions larger than 500 nm. In embodiments, the first sensor cavity may comprise a first electrolyte solution and/or the second sensor cavity may comprise a second electrolyte solution. In embodiments, sensing an analyte using the field-effect transistor sensor may comprise moving the analyte from the first sensor cavity (i.e. from the 'cis' side of the FET sensor), through the nanopore, towards the second sensor cavity (i.e. towards the 'trans' side of the FET sensor). In embodiments where the nanopore is defined as an opening in the FET channel and in one or more overlaying layers, the channel region may be closer to the second orifice than to the first orifice. In embodiments, the channel region (or particularly the conductive channel therein) may be at a distance of from 0 to 5 nm of the second orifice. One way to influence the position of the conductive channel within the channel region is by doping more a part of the channel region to increase the tendency of the conductive channel to form there. Doping more means either that one part is doped while the other is not or that one part is doped with a first doping concentration while another part is doped more with a second, higher, doping concentration.

In embodiments, the channel region may comprise a top portion and a bottom portion wherein the top portion is closer to the first orifice of the nanopore than is the bottom portion, and wherein the bottom portion is doped more than the top portion. This is advantageous because this increases the sensitivity of the sensor.

In embodiments, the channel region may comprise a top portion and a bottom portion wherein the top portion comprises the first orifice of the nanopore and the bottom portion comprises the second orifice of the nanopore, and wherein the bottom portion is more doped than the top portion.

In embodiments, the bottom portion may represent 5% or less of the thickness of the channel region.

In embodiments, the channel region may comprise:
ia. a first channel region portion comprising the nanopore, and
ib. a second channel region portion not comprising the nanopore; and
wherein
the first channel region portion has a doping concentration which is at least 2 times lower (e.g. up to 100 times lower) than a doping concentration of the second channel region portion, and/or
the first channel region portion has a bandgap which is at least 5% smaller (e.g. up to 90% smaller) than a bandgap of the second channel region portion.

In embodiments, the length of the first channel region portion may be from 1% to 50% of the channel region length. In embodiments, the length of the first channel region portion may be from 10 nm to 500 nm. In embodiments, a minimum distance between an edge of the first channel region portion and the nanopore comprised in said portion may be at least from 1 to 100 nm. By having the lower doping concentration and/or smaller bandgap in the first channel region portion, a channel current through the channel region may be dominated by the characteristics of the said first portion. A change in this first portion, e.g. in the nanopore, will then result in a larger change of the channel current. In turn, the sensitivity of the nanopore FET for sensing an analyte in the nanopore is thus advantageously increased.

It was surprisingly found within the present invention that the change ($\Delta V$) of a non-linear potential profile in a FET sensor between a filled state of the nanopore (i.e. containing an analyte) and an empty state of the nanopore (i.e. containing a fluid, but no analyte) is relatively large (cf. example 3). Conversely, such a change is comparatively absent for a linear potential profile. It was therefore found particularly advantageous to make a nanopore FET sensor based on a nanopore which is inherently adapted for creating a non-linear potential profile between the first and second orifice (i.e. along an axis between the first and second orifice). Various possibilities exist for designing such a nanopore. In preferred embodiments, the nanopore may be an asymmetric nanopore. Asymmetric nanopores, whether they be asymmetric due to their general shape, due to the composition of the materials delimiting them or a combination thereof (cf. infra), typically advantageously yield nanopore FET sensors with a non-linear potential profile between the first and second orifice. In embodiments, the nanopore may be a symmetric nanopore. The above notwithstanding, some symmetric nanopores may also yield nanopore FET sensors with an asymmetric potential profile between the first and second orifice; for example, an hourglass-shaped nanopore. These nanopores may, however, be less preferred, as the change ($\Delta V$) between the filled and empty state may typically be smaller for these symmetric nanopores. Furthermore, non-linear potential profiles created by symmetric nanopores often comprise an inflexion point at which there is no change between the empty and the filled state. In that case, it typically becomes particularly advantageous to control at which point along the nanopore the sensing is performed, in order to avoid said inflexion point.

In embodiments, the first orifice may differ from the second orifice thereby creating the non-linear potential profile between the first and second orifice. When the first orifice differs from the second orifice, an asymmetric nanopore is advantageously straightforwardly obtained.

In embodiments, the cross-section of the nanopore may vary along the axis going from the first to the second orifice. This variation may be continuous or step-wise. In embodiments, the first orifice and the second orifice may differ in area and/or may be delimited by edges differing in chemical nature. In embodiments, the area of the first orifice may be larger than the area of the second orifice. In preferred embodiments, a larger degree of asymmetry may be created by combining e.g. an asymmetric shape of the nanopore with an asymmetric composition of the materials delimiting the nanopore. In such a case, the obtainable change ($\Delta V$) between the filled and empty state may typically be increased.

The nanopore is typically oriented at an angle ($\beta$) to the source-drain axis. The angle may for example be from 30 to 150°, preferably from 60 to 120°, more preferably from 85 to 95°, most preferably 90°. In embodiments, the nanopore may have a width (w) of from 1 to 150 nm. In embodiments, the nanopore may have a smallest width (e.g. at the second orifice) of from 1 to 20 nm, preferably from 2 to 10 nm, yet more preferably from 5 to 7 nm. Thinner nanopores (e.g. 10 nm or smaller) may advantageously yield a higher sensitivity. In embodiments, the nanopore may have a largest width (e.g. at the first orifice) of from 1 to 150 nm, preferably from 2 to 100 nm, yet more preferably from 5 to 40 nm. In embodiments, the nanopore may have a height (h) of from 1 to 150 nm, preferably from 5 to 100 nm, yet more preferably from 10 to 50 nm, such as 20 nm. Higher nanopores may advantageously yield a higher sensitivity. The nanopore typically comprises a first orifice corresponding to an opening on a first side towards a first sensor cavity (e.g. towards a first electrolyte solution) and a second orifice corresponding to an opening towards a second sensor cavity (e.g. towards a second electrolyte solution). The first and the second orifice may typically have any shape, such as triangular, rectangular, square, oval, circular, irregular, etc.

In embodiments, the nanopore may taper from the first orifice towards the second orifice. In embodiments, an average inclination ($\alpha$) of a tapered sidewall of the nanopore may be from 1 to 100°, preferably from 5 to 80°, such as 70°, preferably from 5 to 45°, such as 37°, yet more preferably from 5 to 15°, such as 10°. In embodiments, the nanopore may taper smoothly (e.g. continuously) from the first orifice towards the second orifice (e.g. having the shape of a truncated cone, truncated pyramid or truncated hemisphere), or the nanopore may comprise a step-profile (e.g. a profile comprising one or more step-like discontinuities).

In embodiments, the first orifice and the second orifice may be delimited by edges of different permittivity and/or different surface charge.

In embodiments, the permittivity and/or the surface charge may vary along the axis going from the first orifice to the second orifice. This variation may be continuous or step-wise. Preferably, the charge becomes more positive or less negative from the first orifice to the second orifice. In embodiments, the first orifice may be delimited by an edge formed of a first gate dielectric layer and the second orifice may be delimited by an edge formed of a second gate dielectric layer, the first gate dielectric layer having a chemical composition (e.g. translating in a different permittivity) differing from a chemical composition of the second gate dielectric layer and/or the first gate dielectric layer having a thickness differing from a thickness of the second gate dielectric layer.

In embodiments, the permittivity and/or the thickness of the dielectric layer may vary along the axis going from the first orifice to the second orifice. This variation may be continuous or step-wise. In embodiments, the first dielectric layer having the thickness differing from the thickness of the second dielectric layer may have a chemical composition in common with the second dielectric layer or may have a composition differing therefrom. In embodiments, the first and/or second dielectric layer may be made of a material selected from $SiO_2$, $Si_3N_4$, $Al_2O_3$, $HfO_2$, $TiO_2$ and $Ta_2O_5$. In embodiments, the first dielectric layer may consist of $SiO_2$ and the second dielectric layer may consist of $Al_2O_3$.

A practical way to have the edges of the first and second orifices differing in their chemical nature is by lining the nanopore with a first gate dielectric layer, thereby forming the edge of the first (or second) orifice and coating the surface comprising the second (or first) orifice with a second gate dielectric layer, thereby forming the edge of the second (or first) orifice. This way, the thickness of the first gate dielectric layer (measured parallelly to the substrate surface, and typically perpendicularly to the axis going from the first orifice to the second orifice if this axis is at a 90° angle with the substrate surface) is also much smaller than the thickness of the second gate dielectric layer, which is advantageous.

In embodiments, the first orifice and the second orifice may be delimited by edges differing in their surface chemical functionalization. In embodiments, the surface functionalization may vary along the axis going from the first orifice to the second orifice. This variation may be continuous or step-wise. In embodiments, the first orifice and/or the second orifice may be functionalized with a self-assembling monolayer (SAM). In embodiments, the self-assembling monolayer may be bonded to the dielectric layer (e.g. first or second dielectric layer). In embodiments, the first orifice may have the surface chemical functionalization which is more positively or more negatively charged than the surface chemical functionalization of the second orifice, preferably more negatively. While any difference between the surface charging of the orifices is typically advantageous, a larger improvement in sensitivity may be observed when the first orifice is negatively charged. The surface chemical functionalization of the first orifice may, for example, be acidic (e.g. comprising —COOH groups), while the surface chemical functionalization of the second orifice may be neutral. Alternatively, the surface chemical functionalization of the first orifice may be neutral, while the surface chemical functionalization of the second orifice may be basic (e.g. comprising —$NH_3$ groups). In preferred embodiments, the surface chemical functionalization of the first orifice may be acidic (e.g. comprising —COOH groups), while the surface chemical functionalization of the second orifice may be basic (e.g. comprising —$NH_3$ groups). In embodiments, the first dielectric may consist of $SiO_2$ selectively coated with a silane (e.g. comprising —COOH groups) and the second dielectric may consist of $Al_2O_3$ selectively coated with a phosphoric acid derivative (e.g. comprising —$NH_3$ groups). In embodiments, these chemical functionalization differences expressed for the first and second orifice may be expressed as differences along the axis going from the first orifice to the second orifice. These variations may be continuous or step-wise.

In embodiments, the nanopore field-effect transistor sensor may further comprise one or more side gates, the side gates laterally positioned with respect to the channel region. The one or more side gates can advantageously be used to align the conductive channel inside the channel region, by applying a voltage across the one or more side gates. Some degree of misalignment of the conductive channel with respect to the nanopore can thereby be rectified, advantageously increasing the interaction between both.

In embodiments, any feature of any embodiment of the first aspect may independently be as correspondingly described for any embodiment of any of the other aspects.

In a second aspect, the present invention relates to a nanopore field-effect transistor sensor array, comprising at least 50 nanopore field-effect transistor sensors according to any embodiment of the first aspect, preferably at least 100, yet more preferably at least 1000.

Nanopore field-effect transistors in accordance with the present invention can advantageously be made in relatively large numbers on a same substrate, which can allow a high degree of parallelization and/or a high throughput. Furthermore, they can be made using techniques that are compatible with current CMOS technology and can be integrated therewith in the same device.

In embodiments, any feature of any embodiment of the second aspect may independently be as correspondingly described for any embodiment of any of the other aspects.

In a third aspect, the present invention relates to a system comprising:
  i. the nanopore field-effect transistor sensor according to any embodiment of the first aspect,
  ii. a first electrolyte solution contacting the first orifice of the nanopore (e.g. at a 'cis' side of the channel region), and
  iii. a second electrolyte solution contacting the second orifice of the nanopore (e.g. at a 'trans' side of the channel region).

In embodiments, the first electrolyte solution may have an ionic strength differing from an ionic strength of the second electrolyte solution. In embodiments, the first and/or second electrolyte solution may be a solution of a water-soluble salt. In embodiments, the ionic strength difference may be due to a difference in electrolyte charge (e.g. KCl vs. $CaCl_2$ vs. $FeCl_3$), concentration (e.g. 1 M vs. 1 mM) and/or mobility (e.g. e.g. LiCl vs. KCl) in the first electrolyte solution compared to the second electrolyte solution. Two different electrolyte solutions advantageously add another level of asymmetry to the nanopore FET system, thereby increasing the observable change ($\Delta V$) in the potential profiles. In embodiments, a concentration of the electrolyte in the first and/or second electrolyte solution may be from 1 µM to 10 M, preferably from 1 mM to 1 M.

In embodiments, any feature of any embodiment of the third aspect may independently be as correspondingly described for any embodiment of any of the other aspects.

In a fourth aspect, the present invention relates to a method for forming a nanopore field-effect transistor sensor, comprising:
  a. providing a structure comprising:
    i. a substrate,
    ii. a source region and a drain region in the substrate, defining a source-drain axis;
    iii. a channel region between the source region and the drain region,
    iv. optionally a layer on the channel region, and
    v. a mask layer over the channel region and the optional layer, the mask layer comprising an opening therein overlaying the channel region, the opening having a first width and being oriented at an angle to the source-drain axis;
  b. optionally, shrinking the opening such that the first width is reduced to a second width;
  c. etching the optional layer if present and the channel region through the opening, thereby forming a nanocavity;
  d. optionally, shrinking a width of the nanocavity.

e. optionally, removing the mask layer;
f. forming the nanopore from the nanocavity by opening the substrate underneath the nanocavity; the nanopore having a first orifice delimited by a first edge and a second orifice delimited by a second edge;

wherein the nanopore is adapted for creating a non-linear potential profile between the first and second orifice by:

performing step c of etching the channel region through the opening by anisotropically etching the channel region and the optional layer if present in such a way that the first orifice and the second orifice differ in area, and/or by modifying the first edge and/or the second edge so that they differ in chemical nature and/or so that they are made of dielectric material differing in thickness.

In embodiments, if no optional layers are present, the nanocavity referred to in step c, d and f, is defined as an opening in the channel region.

In embodiments where optional layers are present, the nanocavity may be defined either as the opening in the channel region or as the opening in the channel region and the optional layers. In embodiments where optional layers are present and the nanocavity is defined as the opening in the channel region, the part of the opening extending in the optional layers is not considered part of the nanocavity.

The substrate is most typically a semiconductor substrate such as a group IV substrate (e.g. an Si substrate).

While methods in accordance with the fourth aspect may be preferred, it will be clear that other methods can exist for fabricating embodiments of the first, second and/or third aspect.

The optional layer is preferably a dielectric layer.

In embodiments, the first and the second edges may differ in chemical nature by virtue of differing in surface chemical functionalization.

In embodiments, the channel region may be made of silicon.

In embodiments, step b may be performed using atomic layer deposition or sequential infiltration synthesis.

In embodiments, step d may be performed using selective epitaxial growth.

In embodiments, any feature of any embodiment of the fourth aspect may independently be as correspondingly described for any embodiment of any of the other aspects.

In a fifth aspect, the present invention relates to a use of a non-linear potential profile for increasing a sensitivity and/or a spatial resolution of a nanopore field-effect transistor sensor.

In embodiments, the sensitivity may relate to a change in potential difference (e.g. between a filled state and an empty state; $\Delta V$). The change in potential difference may for example be measured through a change in the measured channel current. In embodiments, the potential difference may be normalized (e.g. by dividing the potential difference by the measured potential in the empty state).

In embodiments, any feature of any embodiment of the fifth aspect may independently be as correspondingly described for any embodiment of any of the other aspects.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example 1

Fabrication of an Asymmetric Nanopore Field-Effect Transistor Sensor

We now refer to FIG. 1. A field-effect transistor (FET) structure (110) is first provided comprising a substrate (200) comprising a buried oxide layer (202; e.g. $SiO_2$) on a support layer (201), a channel region (330) on the buried oxide layer (202) in-between two source/drain regions (310,320), source/drain contacts (311,321) to the source/drain regions (310,320) and a dielectric layer (340) conformally covering the channel region (330), source/drain regions (310,320) and source/drain contacts (311,321). This FET structure (110) may be made based on methods which are well-known in the art.

Figure 2:
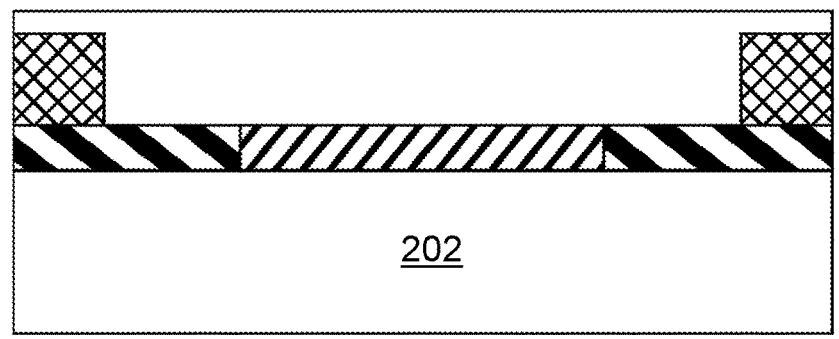

We now refer to FIG. 2. A deep (e.g. around 50 to 100 µm deep) dry or wet etching is performed to open the bottom of the buried oxide layer (202), through the support layer (202). A freestanding FET structure is thereby obtained.

Figure 3:
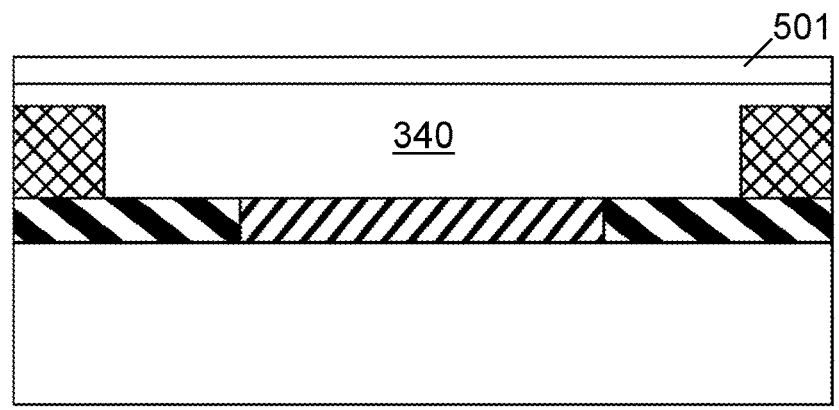

We now refer to FIG. 3. A hardmask layer (501) (e.g. $Al_2O_3$) is deposited over the dielectric layer (340), as part of a mask layer (500).

Figure 4:
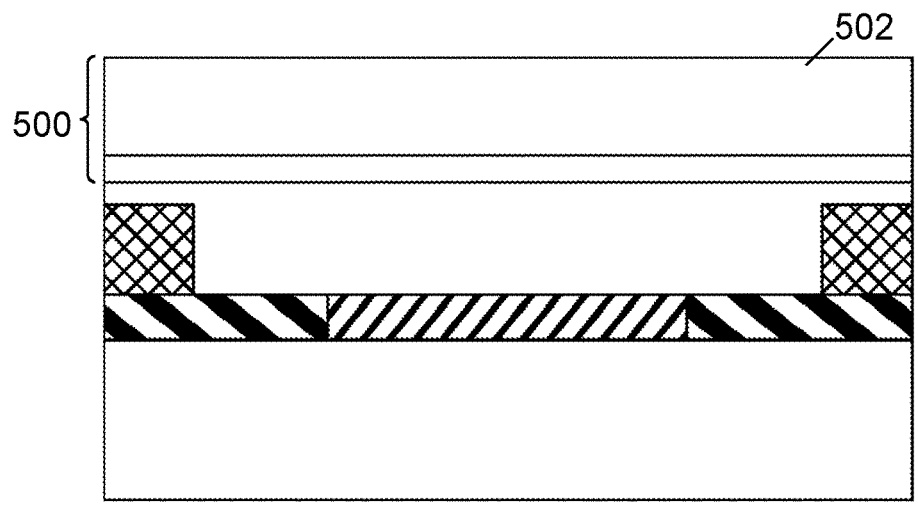

We now refer to FIG. 4. A photoresist layer (502; e.g. poly(methyl methacrylate)), as part of the mask layer (500) is spin coated over the hardmask layer (501).

Figure 5:
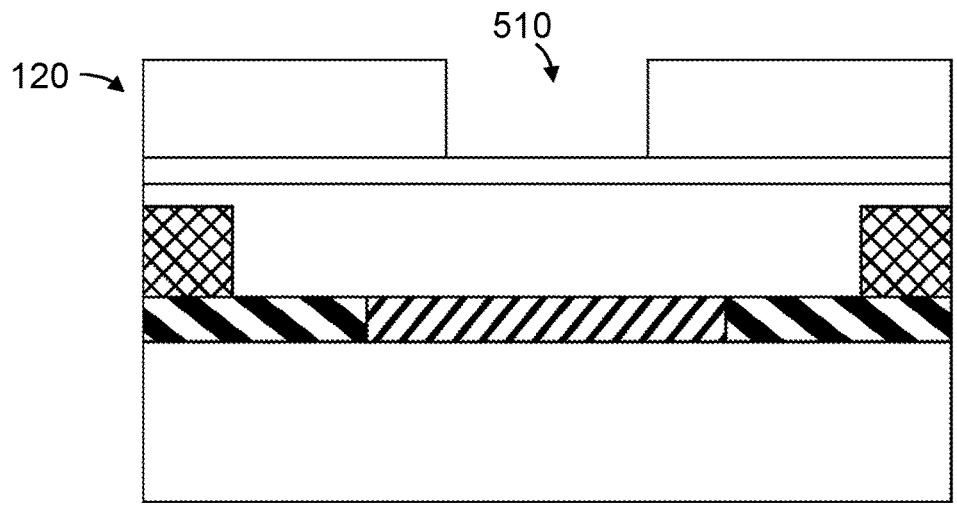

We now refer to FIG. 5. A small opening (510), e.g. around 20 nm wide, is patterned into the photoresist layer (502), for example using electron-beam lithography, to obtain an intermediate structure (120).

Figure 6:
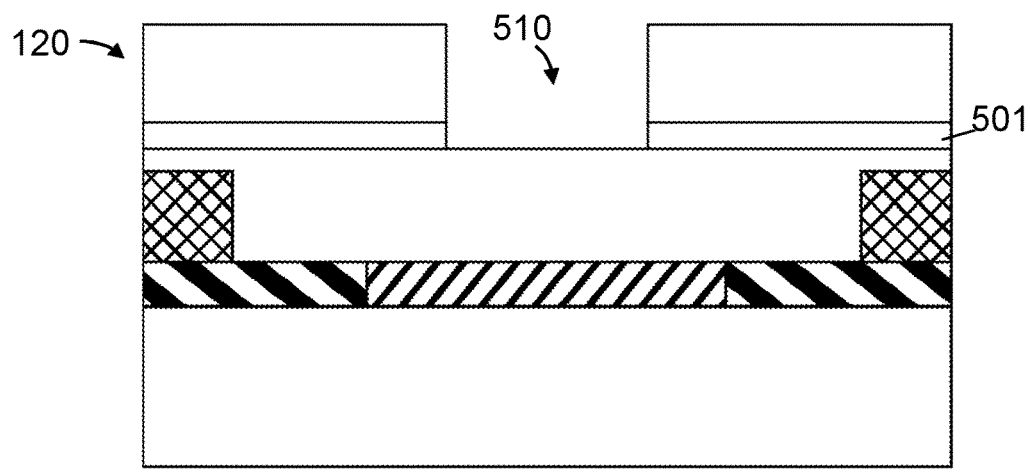

We now refer to FIG. 6. The opening (510) is patterned down into the hardmask layer (501) using a dry or wet etching.

Figure 7:
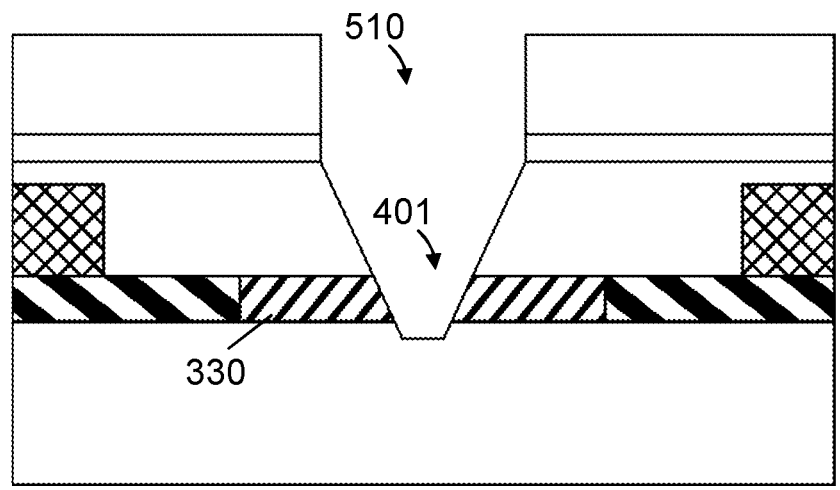

We now refer to FIG. 7. The opening (510) is patterned down through the dielectric layer (340) and the channel region (330) using a dry or wet etching; forming a nanocavity (401) in the channel region (330). The etching is performed in such a way that the width of the nanocavity (401) tapers down towards the bottom of the nanocavity (401).

As an alternative to patterning the small opening directly (as shown in FIG. 5) and transferring it down through the channel region (as shown in FIGS. 6 and 7), a larger opening, e.g. around 40 nm wide, may first be made, for example using deep ultraviolet lithography. This opening may then subsequently be shrunk (e.g. to around 20 to 24 nm) prior to transferring it into the channel region (not shown in the figures). Shrinking said opening may, for example, be achieved by conformally depositing a further mask lining into the opening, e.g. by atomic layer deposition (ALD), thereby reducing one or more lateral dimensions of the opening (not shown in these figures). To this end, the opening may for example first be transferred into the hardmask before shrinking it. Alternatively, shrinking said opening may, for example, also be achieved by forming the further mask lining using sequential infiltration synthesis (SIS). In that case, SIS can, for example, be performed on the photoresist itself, before transferring down the opening.

Figure 8:
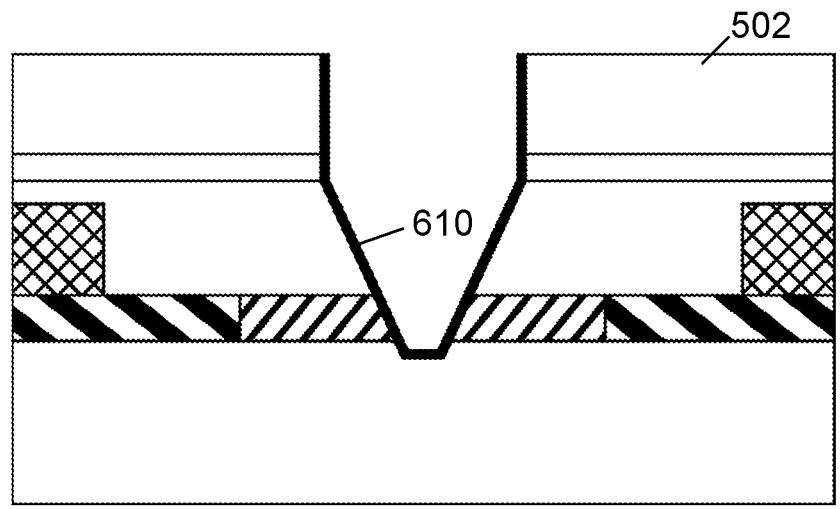

We now refer to FIG. 8. At least the nanocavity (401) is conformally lined with a first gate dielectric (610; e.g. $SiO_2$), for example using ALD.

Figure 9:
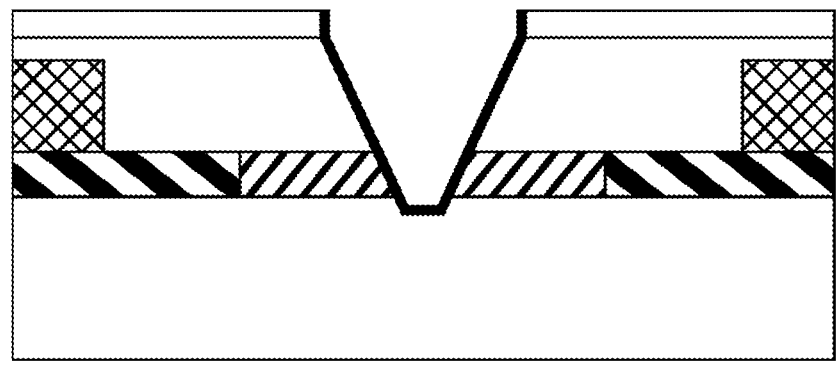

We now refer to FIG. 9. The photoresist layer (502) is removed.

Figure 10:
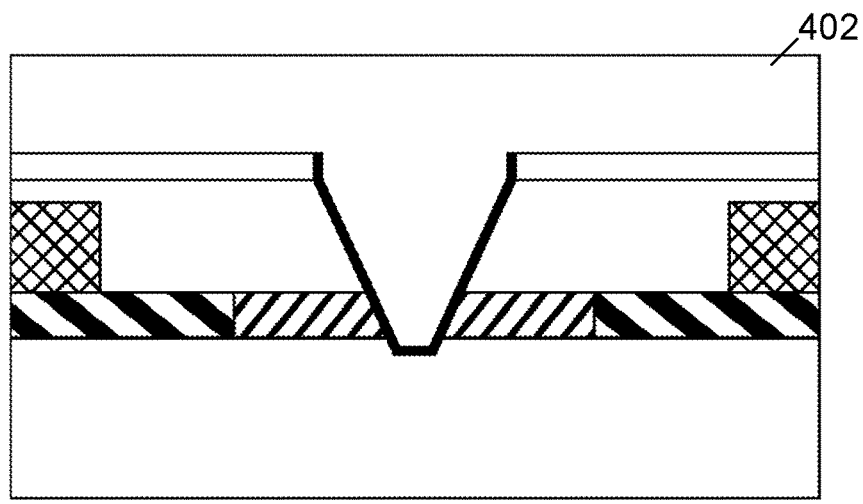

We now refer to FIG. 10. The nanocavity (401) is filled with a protective material (402; e.g. a resist, a porous material or a solid-state material), in order to safeguard it during the subsequent process steps.

Figure 11:
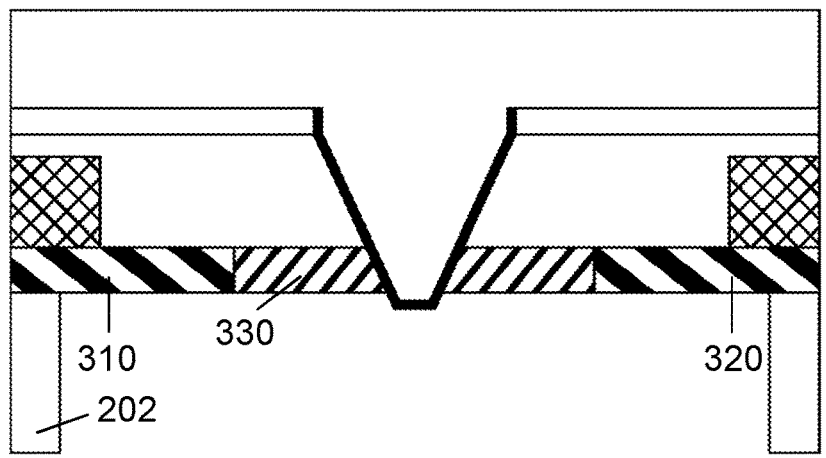

We now refer to FIG. 11. At least part of the buried oxide layer (202) is removed, thereby opening a bottom surface of the channel region (330) and, optionally, of the source/drain regions (310,320).

Figure 12:
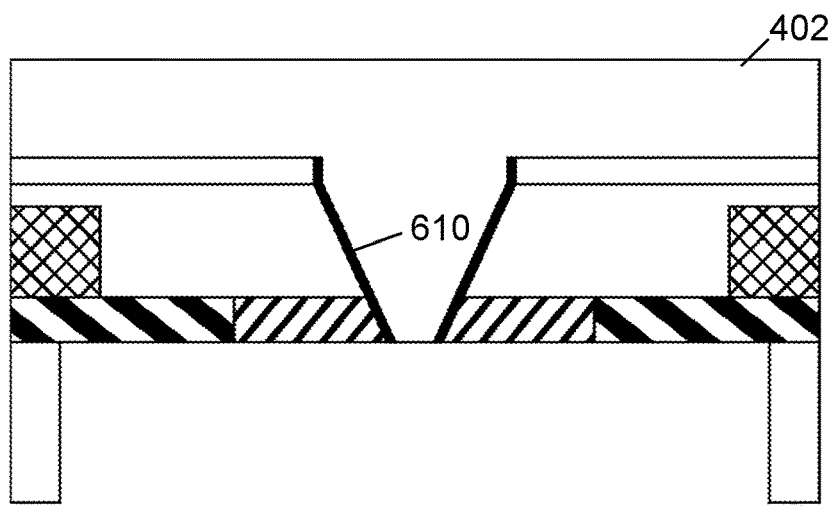

We now refer to FIG. 12. Using a dry or wet etching, the portion of the first gate dielectric (610) extending below the channel region (330) is removed.

Figure 13:
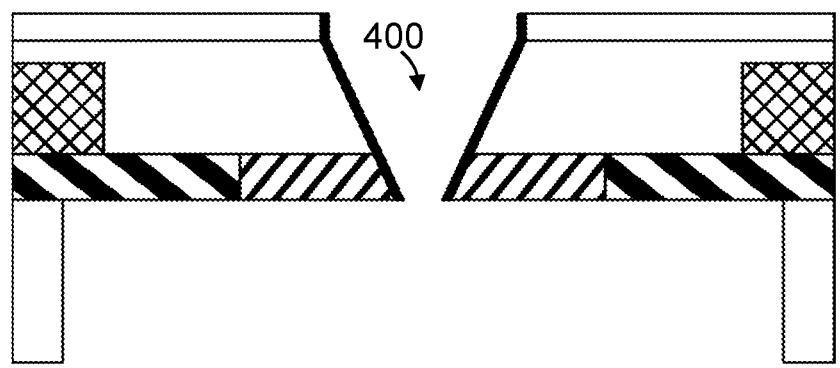

We now refer to FIG. 13. The protective material (402) is removed to open up the nanopore (400).

Figure 14:
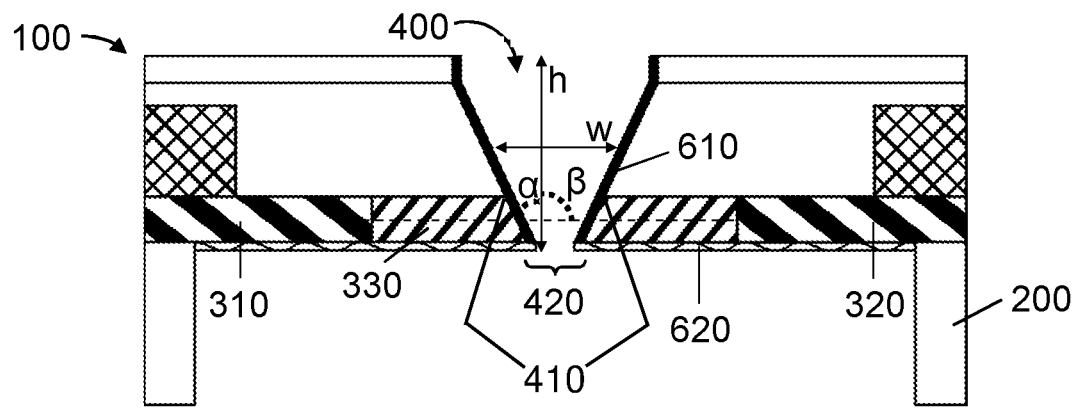

We now refer to FIG. 14. Using ALD, evaporation or sputtering, a second gate dielectric (620; e.g. $Al_2O_3$) is deposited on a bottom surface of the channel region (330) and, optionally, of the source/drain regions (310,320). A nanopore FET sensor (100) is thereby obtained, wherein the first orifice (410) of the nanopore (400) is delimited by the first gate dielectric (610) and the second orifice (420) is delimited by the second gate dielectric (620).

Optionally, additional asymmetry may be created by selectively functionalizing one or both of the gate dielectrics. $SiO_2$ may, for example, be selectively coated with a silane comprising —COOH groups, while $Al_2O_3$ may be selectively coated with a phosphoric acid derivative comprising —$NH_3$ groups.

Yet further asymmetry can optionally be introduced in the measuring system, by contacting a first electrolyte solution to a first (e.g. 'cis') side of the nanopore FET sensor and contacting a second electrolyte solution to the second (e.g. 'trans') side of the nanopore FET sensor, wherein the first and second electrolyte solution differ in ionic strength. The difference in ionic strength can be achieved in several ways, e.g. by having a different concentration (e.g. 1 M vs. 1 mM), ionic charge (e.g. KCl vs. $CaCl_2$ vs. $FeCl_3$) and/or mobility (e.g. LiCl vs. KCl) of electrolytes on the first side with respect to the second side.

Example 2

Various Asymmetric Nanopore Architectures Suitable for Creating a Non-Linear Potential Profile The architecture of a nanopore can typically be decomposed into at least the vertical profile of the nanopore and the shape of its orifices.

Figure 15:
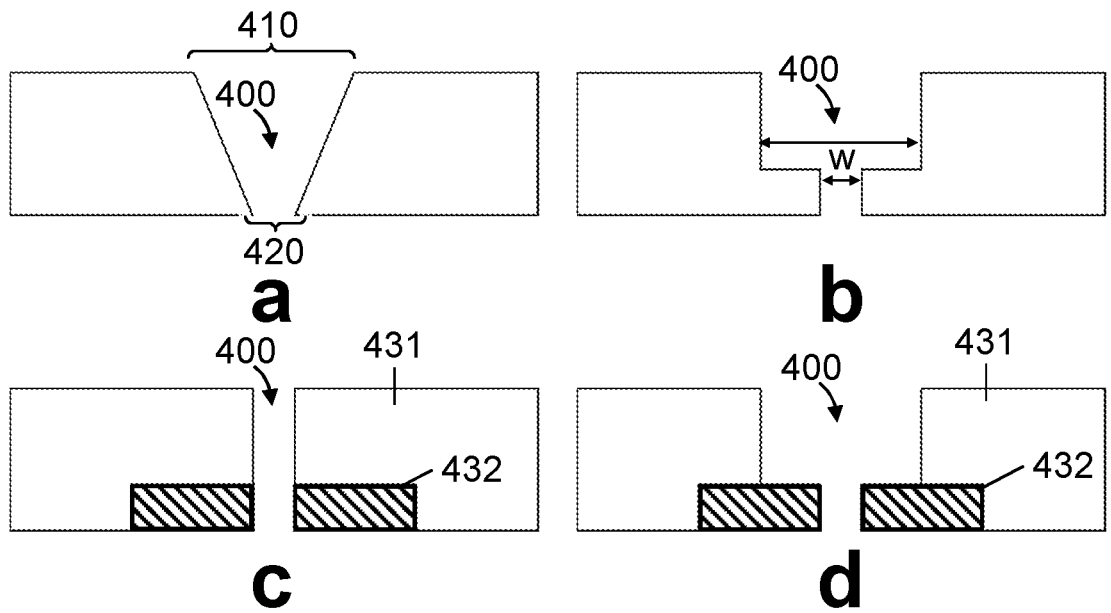
FIG. 15, parts a-d, shows vertical cross-sections through channels in accordance with exemplary embodiments of the present invention.

We now refer to FIG. 15, parts a-d, showing vertical cross-sections of various exemplary asymmetric nanopore (400) profiles in accordance with embodiments of the present invention. In FIG. 15, part a, a nanopore (400) having a width which tapers uniformly from the first orifice (410) to the second orifice (420) is shown. In FIG. 15, part b, a nanopore (400) with a step-profile is shown; e.g. the width (w) of the nanopore (400) may have one or more discrete locations at which the nanopore width changes, but said width may otherwise be relatively constant. In FIG. 15, part c, a nanopore (400) is shown having a constant width, but comprising subcomponents (431,432) of differing composition; the subcomponents (431,432) may, for example, have a difference in permittivity. While the subcomponents (431, 432) shown here both extend substantially beyond the nanopore surface, the different composition may in embodiments also be limited to a difference at the nanopore surface. For example, one material may define the nanopore (400), but it may comprise a first region defining a first portion of the nanopore (400) and having one surface chemical functionalization (e.g. its native surface functionalization), and a second region defining another portion of the nanopore (400) and having a differing surface chemical functionalization (e.g. a non-native surface functionalization). In FIG. 15, part d, a nanopore (400) with a step-profile similar to FIG. 15, part b is shown, but wherein said step-profile is due to the presence of different subcomponents (431,432) akin to FIG. 15, part c. A nanopore (400) in accordance with FIG. 15, part d may, for example, be obtained by performing a selective epitaxial growth (e.g. selective epitaxial growth of Si) on a subcomponent of one composition (432), selectively with respect to a subcomponents of a different composition (431); thereby obtaining a change in width along the nanopore (400).

Figure 16:
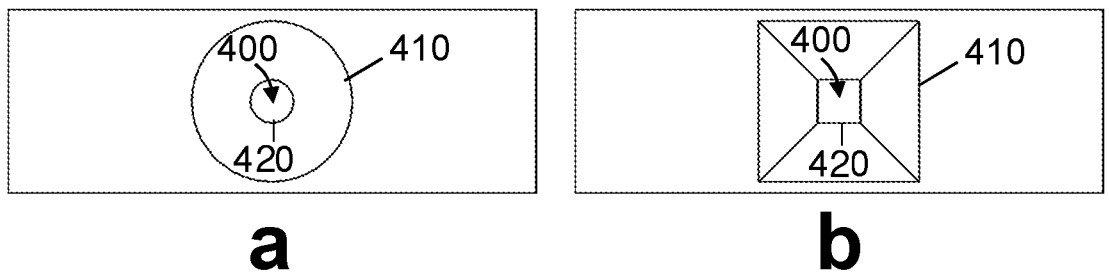
FIG. 16, parts a and b, shows top views of nanopore architectures with different orifice shapes, in accordance with exemplary embodiments of the present invention.

We now refer to FIG. 16, parts a and b, showing top views of exemplary nanopore (400) architectures with different orifice shapes. In FIG. 16, part a, a nanopore (400) having a first (410) and second (420) orifice both having a circular shape is shown. In FIG. 16, part b, a nanopore (400) with a first (410) and second (420) orifice both having a square shape is shown. In other embodiments, which are not depicted, the orifices may have other shapes (e.g. oval, rectangular, polygonal, etc.) and the shape of the first orifice need not be the same as that of the second orifice.

Figure 20:
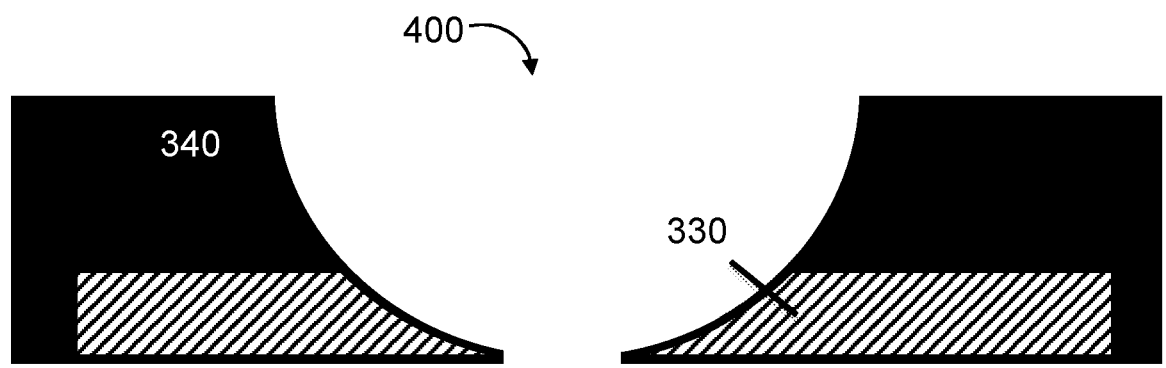
FIG. 20 shows a vertical cross-sections through a channel in accordance with an exemplary embodiment of the present invention.

It will be clear that the orifice shapes and vertical profiles of the nanopore can be combined in a variety of ways to form different nanopore architectures; some examples include:
- a nanopore with a vertical profile as in FIG. 15, part a, and a top view as in FIG. 16, part a, its general shape may thus correspond to that of a truncated cone;
- a nanopore with a vertical profile as in FIG. 15, part a, and a top view as in FIG. 16, part b, its general shape may thus correspond to that of a truncated pyramid;
- a nanopore with a vertical profile as in FIG. 15, part b, and a top view as in FIG. 16, part a, or 16, part b (without the lines connecting the corners of the inner square to the corners of the outer square);
- a nanopore with a vertical profile as in FIG. 20 and a top view as in FIG. 16, part a, its general shape may thus correspond to that of a spherical cap such as an hemisphere,
- a nanopore with a vertical profile as in FIG. 15, part c, and its orifices may be circular or rectangular (corresponding top view not depicted), its general shape may thus correspond to that of a cylinder or cuboid comprising surfaces of different nature;
- a nanopore with a vertical profile as in FIG. 15, part d, and its orifices may be circular or rectangular (corresponding top view not depicted); etc.

Example 3

Effect of a Non-Linear Potential Profile

Figure 17:
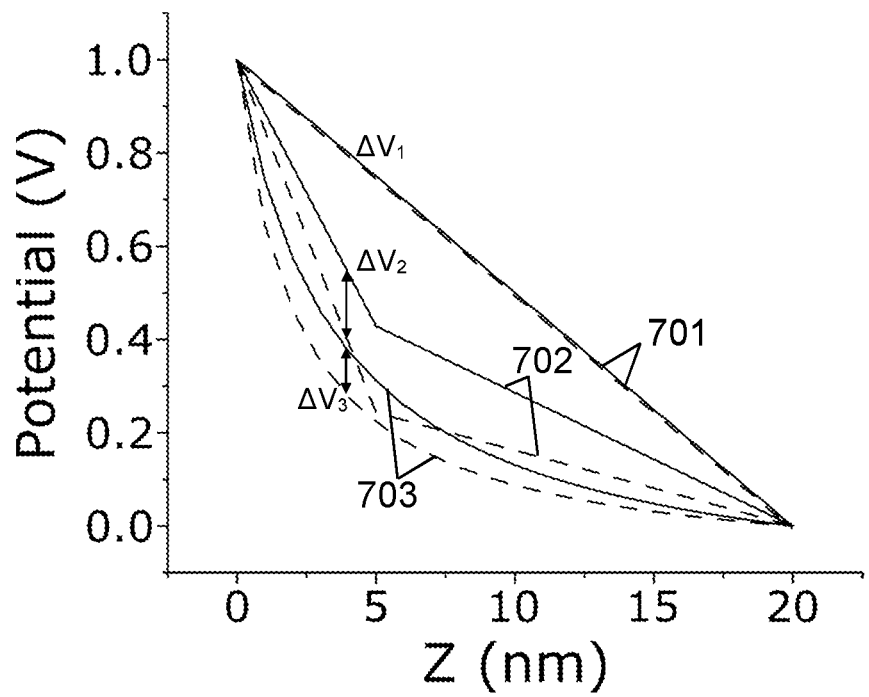
FIG. 17 shows characteristic potential profile curves for three different nanopores, two of which are asymmetric nanopores in accordance with exemplary embodiments of the present invention.

We now refer to FIG. 17, depicting characteristic potential profile curves for 20 nm long nanopores, going from their entrance (i.e. the cis orifice; Z=0 nm) to their exit (i.e. the trans orifice; Z=20 nm). The potential profile (701, 702, 703) of a symmetric nanopore (701) having a uniform width and nature across the entire depth, a step-profile asymmetric nanopore (702) and a uniformly tapering asymmetric nanopore (703) are shown, both in an empty (i.e. containing a fluid, but no analyte; full line) and filled (i.e. containing an analyte; dashed line) state. As shown in FIG. 17, the potential profile of the symmetric nanopore barely differs between the filled state and the empty state (very small $\Delta AV_1$), complicating the detection of the presence of the analyte. Conversely, for both asymmetric nanopores, the potential profile in the filled state is considerably different from that in the empty state (large $\Delta V_2$ and $\Delta V_3$); e.g. a difference of 10% or more, or even 30% or more can be observed. This potential difference is furthermore typically amplified in the FET, thereby yielding a relatively huge change in the channel current between the empty and filled state and greatly facilitating detection of the analyte.

Example 4

Figure 18:
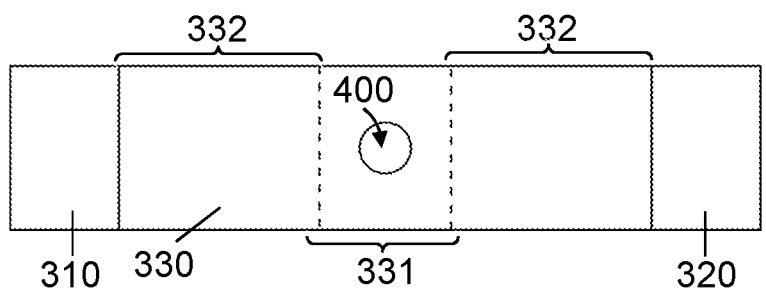
FIG. 18 is a schematically representation of a nanopore FET comprising differing channel region portions, in accordance with exemplary embodiments of the present invention.

Nanopore Field-Effect Transistor Sensor Wherein the Channel Region Comprises Portions with Differing Characteristics We now refer to FIG. 18, schematically depicting a nanopore FET (100) comprising a channel region (330) with a nanopore (400) therein, in-between two source/drain regions (310,320). The channel region (330) comprises a first portion (331) containing the nanopore (400) and two second portions (332), each defined in-between said nanopore-containing portion (331) and a source/drain region (310 or 320). The first portion (331) differs from the second portions (332) in that a doping concentration therein is lower than a doping concentration in the second portions (332). Alternatively, or additionally, the first portion (331) may differ from the second portions (332) in that a bandgap therein is smaller than a bandgap in the second portions (332). The effect of the lower doping concentration and/or smaller bandgap is that the channel current through the channel region (330) predominantly depends on the first portion (331). Any change in this first portion (331), e.g. in the nanopore (400), will thus have an increased effect on the channel current. In turn, the sensitivity of the nanopore FET (100) for sensing an analyte in the nanopore (400) is thereby heightened.

Example 5

Nanopore Field-Effect Transistor Sensor Comprising Side-Gates

When forming the nanopore in the channel region, the nanopore is preferably aligned such that the nanopore runs through the channel of the channel region and interact therewith. However, during manufacture, it may be difficult to ensure that each nanopore is well aligned and some misalignment may nevertheless occur in some devices.

Figure 19:
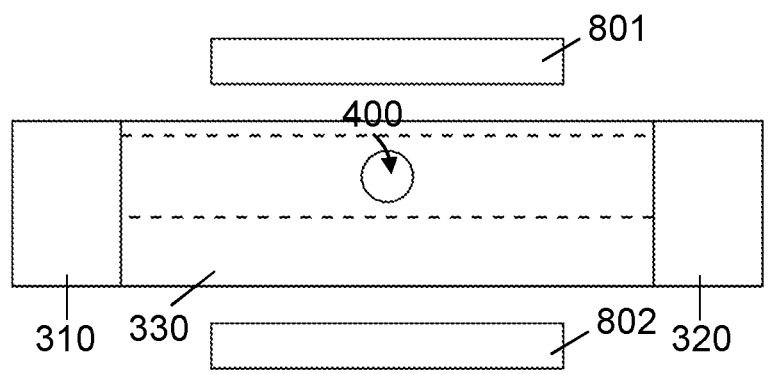
FIG. 19 is a schematically representation of a nanopore FET comprising side gates, in accordance with exemplary embodiments of the present invention.

We now refer to FIG. 19, schematically depicting a nanopore FET (100) comprising a channel region (330) with a nanopore (400) therein, in-between two source/drain regions (310,320); the nanopore (400) being slightly laterally misaligned with respect to the centre of the channel region (330). The nanopore FET (100) additionally comprises two side gates (801,802) laterally positioned with respect to the channel region (330), which can be used to align the channel inside the channel region (330) by applying a voltage across the side gates (801,802). In this way, the side gates (801,802) advantageously allow to correct for a degree of misalignment of the nanopore (400) and can thus increase the interaction between both.

Example 6

Simulations of Nanopore Field-Effect Transistor Sensors

Various simulations with nanopore field-effect transistor sensors having a non-linear potential profile were performed in order to validate their usefulness. It could be confirmed that a singly charged nanocube (1×1×1 nm) and a nanorod (1×1×15 nm) with 15 charges can both be successfully detected; e.g. as a change in the channel current of about 90 nA for the nanocube and about 900 nA for the nanorod, wherein the change is respectively with respect to an equivalent neutral nanocube (e.g. around 1.5 µA) and neutral nanorod (e.g. around 4 µA). Furthermore it was confirmed that the following factors can have a positive effect on the sensitivity: a smaller nanopore width, a higher nanopore, an inclination angle ($\alpha$) between 5 and 80° (preferably between 5 and 45°, for instance between 30 and 45°, such as 37° or more preferably between 5 and 15°, such as 10°), using different gate dielectric compositions (as is e.g. shown in example 1) and using a differently charged gate dielectric surface (wherein the first gate dielectric, on the cis side, is preferably more negatively charged than the second dielectric, on the trans side).

Although preferred embodiments, specific constructions and configurations, as well as materials, have been discussed herein for devices according to the present invention, changes may be made without departing from the technical teachings of this invention. For example, any formulas given above are merely representative of procedures that may be used. Steps may be added or deleted to methods described within the scope of the present invention.

The invention claimed is:

1. A nanopore field-effect transistor sensor, comprising
   i) a source region and a drain region, defining a source-drain axis;
   ii) a channel region between the source region and the drain region; and
   iii) a nanopore defined as an opening in the channel region which completely crosses through the channel region, oriented at an angle to the source-drain axis, and having a first orifice and a second orifice, the nanopore being adapted for creating a non-linear potential profile between the first orifice and second orifice in the channel region.

2. The nanopore field-effect transistor sensor according to claim 1, wherein the first orifice differs from the second orifice thereby creating the non-linear potential profile between the first orifice and second orifice.

3. The nanopore field-effect transistor sensor according to claim 2, wherein the first orifice and the second orifice differ in area and/or are delimited by edges differing in chemical nature.

4. The nanopore field-effect transistor sensor according to claim 3, wherein the nanopore tapers from the first orifice towards the second orifice.

5. The nanopore field-effect transistor sensor according to claim 3, wherein the first orifice and the second orifice are delimited by edges of different permittivity and/or different surface charge.

6. The nanopore field-effect transistor sensor according to claim 5, wherein the first orifice is delimited by an edge formed of a first gate dielectric layer and the second orifice is delimited by an edge formed of a second gate dielectric layer, the first gate dielectric layer having a chemical composition differing from a chemical composition of the second gate dielectric layer and/or the first gate dielectric layer having a thickness differing from a thickness of the second gate dielectric layer.

7. The nanopore field-effect transistor sensor according to claim 5, wherein the first orifice and the second orifice are delimited by edges differing in their surface chemical functionalization.

8. The nanopore field-effect transistor sensor according to claim 1, wherein the channel region comprises:
  ia) a first channel region portion comprising the nanopore, and
  ib) a second channel region portion not comprising the nanopore; and
wherein
  the first channel region portion has a doping concentration which is at least 2 times lower than a doping concentration of the second channel region portion, and/or
  the first channel region portion has a bandgap which is at least 5% smaller than a bandgap of the second channel region portion.

9. The nanopore field-effect transistor sensor according to claim 1, further comprising one or more side gates, the side gates being laterally positioned with respect to the channel region.

10. The nanopore field-effect transistor sensor according to claim 1, further comprising a layer on the channel region.

11. The nanopore field effect transistor sensor according to claim 10, wherein the opening defining the nanopore further extends at least partly through the layer.

12. A nanopore field-effect transistor sensor array, comprising at least 50, at least 100 or at least 1000 nanopore field-effect transistor sensors according to claim 1.

13. The nanopore field-effect transistor sensor according to claim 4, wherein the first orifice and the second orifice are delimited by edges of different permittivity and/or different surface charge.

14. The nanopore field-effect transistor sensor according to claim 13, wherein the first orifice is delimited by an edge formed of a first gate dielectric layer and the second orifice is delimited by an edge formed of a second gate dielectric layer, the first gate dielectric layer having a chemical composition differing from a chemical composition of the second gate dielectric layer and/or the first gate dielectric layer having a thickness differing from a thickness of the second gate dielectric layer.

15. A system comprising:
  i) the nanopore field-effect transistor sensor according to claim 1;
  ii) a first electrolyte solution contacting the first orifice of the nanopore; and
  iii) a second electrolyte solution contacting the second orifice of the nanopore.

16. The system according to claim 15, wherein the first electrolyte solution has an ionic strength differing from an ionic strength of the second electrolyte solution.

17. A method for forming a nanopore field-effect transistor sensor, comprising:
  a) providing a structure comprising:
    i) a substrate;
    ii) a source region and a drain region on the substrate, defining a source-drain axis;
    iii) a channel region between the source region and the drain region;
    iv) optionally a layer on the channel region; and
    v) a mask layer over the channel region and the optional layer if present, the mask layer comprising an opening therethrough overlying the channel region, the opening having a first width and being oriented at an angle to the source-drain axis;
  b) optionally, shrinking the opening such that the first width is reduced to a second width;
  c) etching the optional layer if present, and the channel region, through the opening, thereby forming a nanocavity;
  d) optionally, shrinking a width of the nanocavity;
  e) optionally, removing the mask layer; and
  f) forming a nanopore from the nanocavity by opening the substrate underneath the nanocavity; the nanopore having a first orifice delimited by a first edge and a second orifice delimited by a second edge;
  wherein the nanopore is adapted for creating a non-linear potential profile between the first orifice and the second orifice in the channel region by:
    performing step c of etching the optional layer if present and the channel region through the opening by anisotropically etching the channel region, and the optional layer if present, in such a way that the first orifice and the second orifice differ in area, and
    optionally, modifying the first edge and/or the second edge so that they differ in chemical nature and/or so that they are made of dielectric material differing in thickness.

18. The method according to claim 17, wherein the first edge and second edge differ in chemical nature by virtue of differing in surface chemical functionalization.

19. A nanopore field-effect transistor sensor, comprising
  i) a source region and a drain region, defining a source-drain axis;
  ii) a channel region between the source region and the drain region; and
  iii) a nanopore defined as an opening in the channel region which completely crosses through the channel region, oriented at an angle to the source-drain axis, having a first orifice and a second orifice, and being adapted for creating a non-linear potential profile between the first and second orifice in the channel region,
    wherein the first orifice differs from the second orifice thereby creating the non-linear potential profile between the first orifice and second orifice;
    wherein the first orifice and the second orifice differ in area and/or are delimited by edges differing in chemical nature; and
    wherein the nanopore tapers from the first orifice towards the second orifice, wherein the first orifice and the second orifice are delimited by edges of different permittivity and/or different surface charge.

20. The nanopore field-effect transistor sensor according to claim 19, wherein the first orifice is delimited by an edge formed of a first gate dielectric layer and the second orifice is delimited by an edge formed of a second gate dielectric layer, the first gate dielectric layer having a chemical composition differing from a chemical composition of the second gate dielectric layer and/or the first gate dielectric layer having a thickness differing from a thickness of the second gate dielectric layer.

* * * * *